United States Patent [19]

Nowak et al.

[11] 4,150,319

[45] Apr. 17, 1979

[54] ION GATING GRID

[75] Inventors: David J. Nowak, Dexter; James E. Rice; Donald R. Bianco, both of Ann Arbor, all of Mich.

[73] Assignee: The Bendix Corporation, Teterboro, N.J.

[21] Appl. No.: 835,616

[22] Filed: Sep. 22, 1977

[51] Int. Cl.² .......................... H01J 1/46; H01J 1/52; H01J 17/04; H01J 17/12

[52] U.S. Cl. .................................... 313/348; 313/349

[58] Field of Search ................................ 313/348, 349

[56] References Cited

U.S. PATENT DOCUMENTS

| | | | |
|---|---|---|---|
| 1,333,838 | 3/1920 | Csanyi | 313/348 X |
| 2,026,725 | 1/1936 | Baker | 313/348 X |
| 2,736,832 | 2/1956 | Zaphiropoulos | 313/348 X |
| 2,813,214 | 11/1957 | Van Doorn | 313/348 X |
| 3,795,833 | 3/1974 | King et al. | 313/348 |

Primary Examiner—Saxfield Chatmon, Jr.
Attorney, Agent, or Firm—Anthony F. Cuoco

[57] ABSTRACT

A grid gates a stream of ions when a D.C. potential is applied between two sets of interdigitated wires included in the grid to produce a D.C. field. The improved grid disclosed herein contains the two sets of interdigitated wires in a single plane so that the D.C. field is precisely normal to the ion current flow direction to prevent a residual ion current flow when the grid provides the gating effect.

4 Claims, 6 Drawing Figures

ION GATING GRID

BACKGROUND OF THE INVENTION

1. Field of the Invention

This invention relates generally to a grid type device for gating a stream of ions. More particularly, this invention relates to a grid of the type described which gates the stream of ions without a residual or leakage ion current flow.

2. Description of the Prior Art

Many applications such as, for example, ion mobility measurements, require gating or turning off the ion flow for analysis or measurement purposes, as the case may be. This is accomplished by disposing a grid in the ion stream and normal thereto, and electrically energizing the grid to suppress the ion current flow. Prior to the present invention, grids for this purpose have been unable to completely suppress the ion flow and consequently there has been a residual flow of ion current through the grid. This residual flow, or leakage, of ion current results in a background current which may particularly interfere with low level current measurements made for the required purposes.

A typical example of a prior art grid which permits the aforenoted residual ion current flow is known in the art as the Bradbury-Nielsen type. This grid includes two sets of substantially parallel, closely spaced interdigitated wires in separate and distinct planes which are separated by a finite distance. A stream of ions is allowed to flow in a tube or cylinder by establishing a steady D.C. potential gradient along the axis thereof. Then, in order to analyze the nature of the ion stream, the ion flow is momentarily interrupted. This is accomplished by placing the grid constructed as aforenoted in the path of the ion flow and applying a strong D.C. potential between the two sets of wires to produce a D.C. field. This results in cutting off the ion current flow which is normal to the plane of the grid. However, in prior art grids, since the two sets of wires are actually in two planes, the D.C. field produced by the grid is not precisely normal to the direction of the ion current flow and, indeed, may actually have a small component in the direction of said current flow. This results in a small residual ion current flow even during the time when the grid is closed or shut off to accomplish the aforementioned gating affect. The present invention provides a unique structural configuration which obviates this disadvantage.

SUMMARY OF THE INVENTION

This invention contemplates an improved ion gating grid for the purposes described which includes two sets of interdigitated wires in a single plane so that when the D.C. field is produced between the two sets of wires it is precisely normal to the plane of the wires, with no component in the direction of the ion current flow being present. This results in the capability to completely shut off the ion current flow with an improvement in low level current detection and resolution as is desired. The aforenoted is accomplished by providing a ring shaped frame including two concentric series of holes, one of which series of holes is on a larger radius than the other. Each series of holes provides support for a continuous wire which is laced back and forth across the frame. The resulting grid comprises two closely spaced fine wire sets in a single plane that do not touch or overlap at any point and are thus electrically isolated and separated from each other. The grid has the additional advantage of being simpler and less cumbersome in construction than the prior art grids referred to.

The main object of this invention is to provide an improved ion gating grid which is constructed so as to preclude a residual ion current flow through the grid when the grid is closed or in a shutoff state.

Another object of this invention is to provide a grid of the type described which includes two sets of interdigitated wires in a single plane so that a D.C. field produced when a potential is applied between the wires is precisely normal to the plane of the wires.

Another object of the invention is to accomplish the above by supporting the two sets of wires in a series of concentric holes in a ring shaped frame, whereby the wires are laced back and forth across the frame so that both sets of wires are in a single plane.

Another object of this invention is to provide a grid of the type described which is simpler and less cumbersome in construction than grids heretofore known in the art.

The foregoing and other objects and advantages of the invention will appear more fully hereinafter from a consideration of the detailed description which follows, taken together with the accompanying drawings wherein one embodiment of the invention is illustrated by way of example. It is to be expressly understood, however, that the drawings are for illustration purposes only and are not to be construed as defining the limits of the invention.

DETAILED DESCRIPTION OF THE INVENTION

Figure 1:
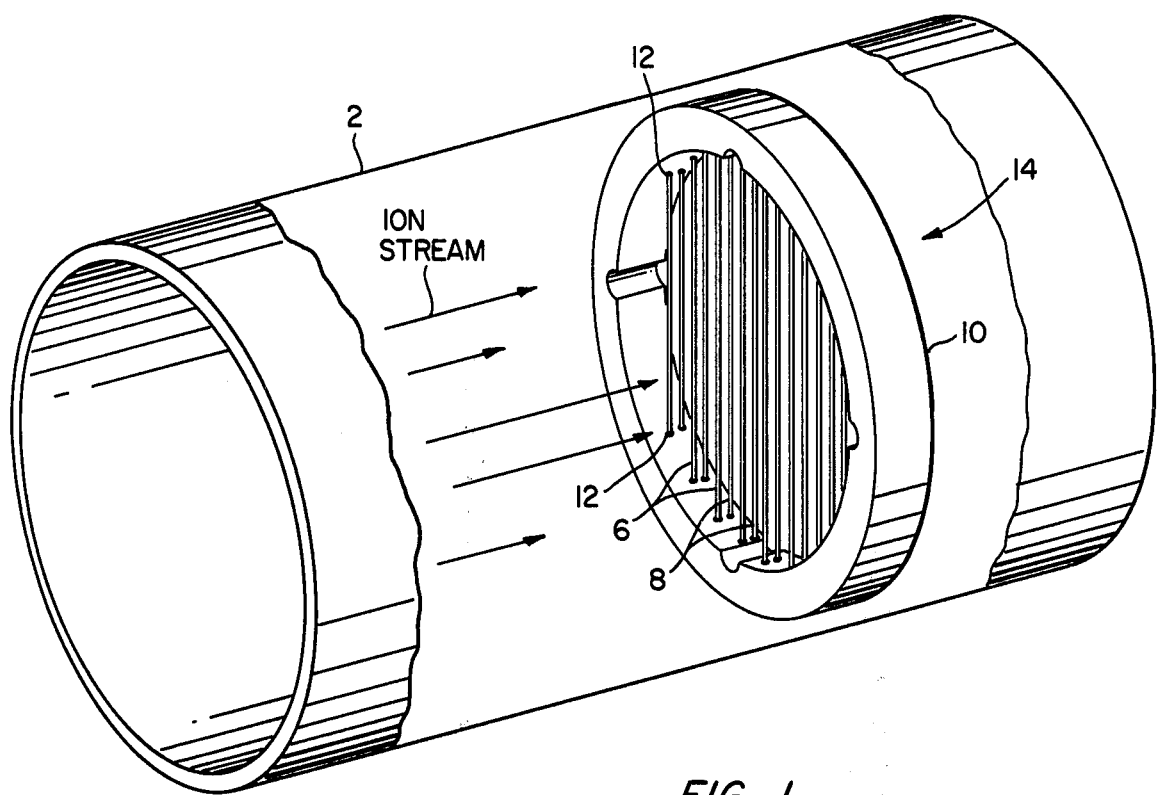
FIG. 1 is an isometric diagrammatic representation illustrating the utilization of an ion gating grid.

The utilization of the invention is best illustrated with reference to FIG. 1. An ion stream is allowed to flow in the direction of the arrows shown in the Figure by establishing a steady D.C. potential gradient along the axis of a tube or cylinder 2 by means (not shown) well known to those skilled in the art.

In order to analyze the nature or make up of the ion stream, the ion stream, i.e., the flow of ions, is momentarily interrupted. This is accomplished by placing a grid designated generally by the numeral 4 in the path of the ion flow and applying a strong D.C. potential between two sets of interdigitated wires. One of the sets of interdigitated wires is designated by the numeral 6, while the other set is designated by the numeral 8.

Figure 2:
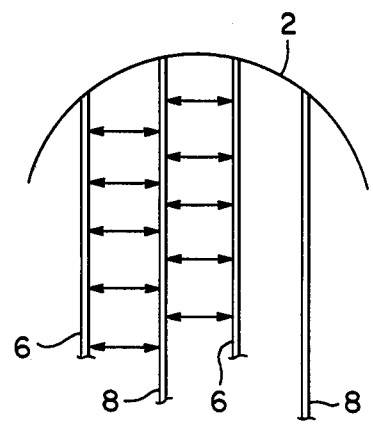
FIG. 2 is a front view diagrammatic representation of the grid shown in FIG. 1 and illustrating a D.C. field produced when a potential is applied between two sets of interdigitated wires included in the grid.

The application of the strong D.C. potential between the two sets of wires by means (not shown) well known in the art produces a D.C. field as illustrated by the arrows in FIG. 2. This results in a reduction of ion current flow normal to the plane of the grid and an ion gating affect is achieved. It is important for accuracy of measurement and analysis, especially when low level ion current measurements are involved, that the D.C. field produced by the grid is precisely normal to the direction of ion current flow.

As heretofore noted, a disadvantage of prior art grids is that the two sets of interdigitated wires 6 and 8 are in different planes so that the D.C. field produced by the grid is not precisely normal or perpendicular to the ion current flow, and inaccuracies result especially when low current measurements are involved. Further, in prior art grid construction the wires are supported on a ring shaped frame 10 by winding the wires around termination points 12 or the like at both ends thereof, and electrically connecting the termination points to an energizing source through a bus or the like. This results in a complicated and cumbersome structural arrangement. The present invention to be next described with reference to FIGS. 3, 4, 5 and 6 overcomes this and other disadvantages as will become evident.

Figure 3:
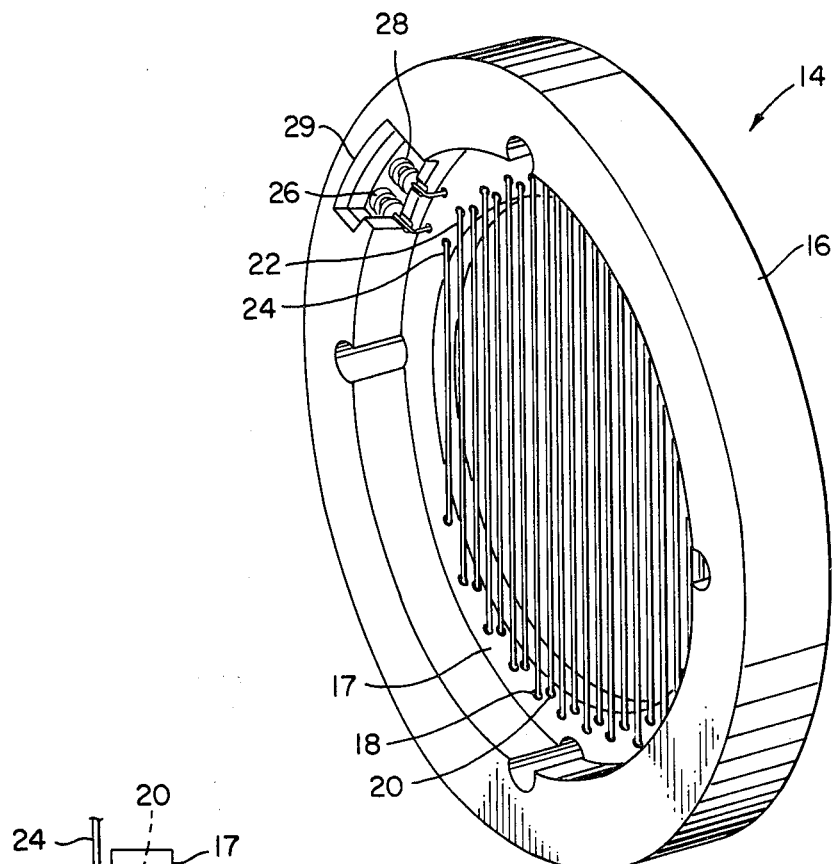
FIG. 3 is an isometric representation of a grid constructed in accordance with the invention.

With reference to FIG. 3, the grid of the invention is designated generally by the numeral 14 and includes a ring shaped frame 16 fabricated from grade A lava that is subsequently fired at a high temperature. This results in an extremely fine grained highly non-porous polished surface which is an insulator with exceptionally high bulk resistivity in the order of $10^{13}$ to $10^{14}$ ohms per centimeter. Further, with a frame fabricated as described, the probability of any static surface charge accumulation with resultant small residual D.C. fields detrimental to the purposes of the invention is significantly reduced.

Two sets of interdigitated wires are wound or laced on the frame. Each set is a continuous wire strand and is laced back and forth between two concentric series of through holes that are accurately drilled around the periphery of a flange 17 on the inside diameter of frame 16. Flange 17 is open at the back as illustrated in FIGS. 5 and 6.

Figure 6:
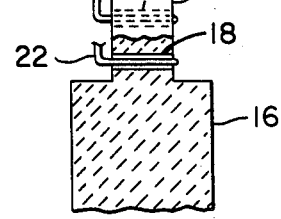
FIG. 6 is a sectioned partial end view of the grid of FIG. 3 and best illustrating the feature of the invention wherein continuous wires are supported on two concentric series of holes, one of which series of holes is on a larger radius than the other.

With reference to FIGS. 3, 4, 5 and 6, one series of concentric holes is designated by the numeral 18 while the other series is designated by the numeral 20. A continuous wire strand 22 is laced in holes 18, while another continuous wire strand 24 is laced in holes 20 as shown in the Figures. Concentric holes 18 are on a larger radius than concentric holes 20 as best shown in FIG. 6, and the holes in each series are disposed intermediate the holes in the other series to provide the aforementioned interdigitated characteristics as shown in the Figures.

Figure 4:
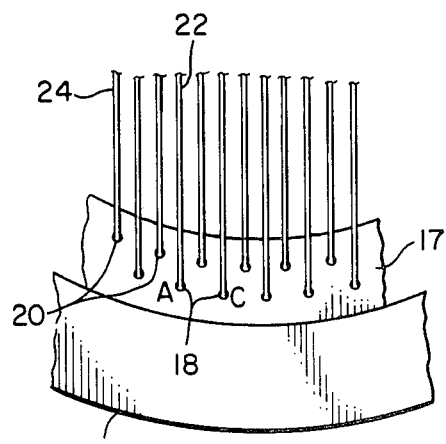
FIG. 4 is a partial front view of the grid of FIG. 3, and illustrating the wire lacing feature of the invention.
Figure 5:
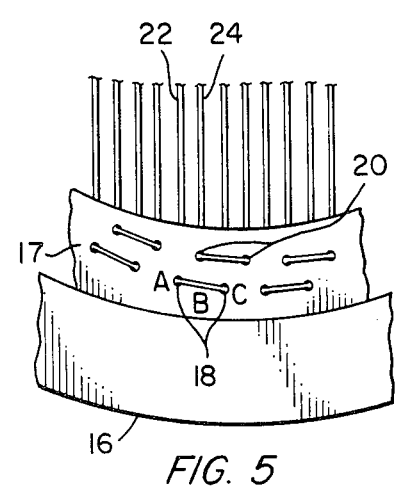
FIG. 5 is a partial rear view of the grid of FIG. 3, and further illustrating the wire lacing feature of the invention.

With reference to FIGS. 4 and 5, it will be seen that continuous wire strand 22 is inserted in holes 18 in flange 17 from the front of the flange at A, laced across the back of the flange at B (FIG. 5) and then laced through the next hole to the front of the flange at C until the wire is laced back and forth across the frame. Continuous wire strand 24 is likewise laced through holes 20 in flange 17. This winding or lacing of two continuous wires 22 and 24 back and forth across the frame results in two sets of closely spaced (0.025 inches between centers) fine wire (0.005 inches in diameter) that do not touch or overlap at any point and are thus electrically isolated and separated from each other.

The configuration of the present invention as shown in FIGS. 3, 4, 5 and 6 has other distinct advantages over prior art ion gating grids. Since continuous wires are used it is not necessary to use a bus to connect the wires to an energizing source as it has heretofore been necessary. With the arrangement shown, the ends of laced continuous wire strands 22 and 24 may be connected to suitable terminals 26 and 28, respectively, included in a terminal block (FIG. 3) connected to an energizing source (not shown). This provides a much simpler and less cumbersome structural arrangement than has heretofore been possible.

Further, in the prior art devices the interdigitated wires are supported on the frame by winding the wires around termination points (terminals or pins) as aforementioned. Ultimately, the wires will sag so as to accentuate the lack of normality or perpendicularity between the planes of the wires and the direction of the ion stream. This condition is obviated by the present invention since the wires may be tightly laced as described with reference to FIGS. 4 and 5 to prevent such sagging and to maintain the required perpendicularity.

It will now be seen that the aforegoing objects of the invention have been attained. An improved ion gating grid is provided which includes two sets of interdigitated wires in a single plane which is precisely normal to the direction of ion current flow, and thereby prevents a residual flow of ions through the grid when the described gating affect is provided.

The unique structural arrangement disclosed results in a grid wherein the two sets of interdigitated wires support an electric field potential of 800 volts/centimeter or greater between the sets of wires. This electrical field intensity is adequate to completely cut off the ion current flow resulting in a measuring or analysis instrument having greater resolution and sensitivity than has heretofore been possible.

Although but a single embodiment of the invention has been illustrated and described in detail, it is to be expressly understood that the invention is not limited thereto. Various changes may also be made in the design and arrangement of the parts without departing from the spirit and scope of the invention as the same will now be understood by those skilled in the art.

What is claimed is:

1. In an ion mobility measurement device, a grid for gating a stream of ions, comprising:
   a ring shaped frame;
   a first series of through holes disposed around the inner periphery of the ring shaped frame at first equal radial distances from the center of said ring;
   a second series of through holes concentric with the first series of holes and disposed around the inner periphery of the ring shaped frame at second equal radial distances from the center of said ring, said second radial distances being greater than said first radial distances;
   a first continuous wire strand laced through the first series of holes;
   a second continuous wire strand laced through the second series of holes; and
   the first and second laced wire strands providing two sets of interdigitated wires in a single plane which is precisely normal to the stream of ions when the grid is disposed in the stream.

2. A grid for gating a stream of ions as described by claim 1, wherein:

each of the first and second continuous wire strands is laced through the first and second series of concentric holes, respectively, by inserting a wire in a hole from the front of the inner periphery of the ring shaped frame, lacing the wire across the back of the inner periphery and inserting the wire in the next hole from the back of the inner periphery until the wires are laced back and forth across the frame.

3. A grid for gating a stream of ions as described by claim 1, wherein:
each of the continuous strands of laced wires terminates in an end for connecting the wire set to a terminal block.

4. A grid for gating a stream of ions as described by claim 1, wherein:
the ring shaped frame carries a flange on the inner periphery thereof; and
the first and second series of holes are disposed around the flange.

* * * * *